(12) United States Patent
Son et al.

(10) Patent No.: US 11,541,097 B2
(45) Date of Patent: Jan. 3, 2023

(54) CRUDE DRUG COMPOSITION FOR PREVENTING OR TREATING RESPIRATORY DISEASES

(71) Applicant: HELIXMITH CO., LTD., Seoul (KR)

(72) Inventors: Mi Won Son, Gyeonggi-do (KR); Min Jung Bae, Jeollabuk-do (KR); Won Woo Lee, Seoul (KR); Doo Suk Lee, Gyeonggi-do (KR)

(73) Assignee: HELIXMITH CO., LTD., Seoul (KR)

( * ) Notice: Subject to any disclaimer, the term of this patent is extended or adjusted under 35 U.S.C. 154(b) by 0 days.

(21) Appl. No.: 16/980,917

(22) PCT Filed: Mar. 15, 2019

(86) PCT No.: PCT/KR2019/003056
§ 371 (c)(1),
(2) Date: Sep. 15, 2020

(87) PCT Pub. No.: WO2019/177424
PCT Pub. Date: Sep. 19, 2019

(65) Prior Publication Data
US 2021/0000905 A1     Jan. 7, 2021

(30) Foreign Application Priority Data

Mar. 16, 2018   (KR) .................. 10-2018-0031150
Mar. 13, 2019   (KR) .................. 10-2019-0028956

(51) Int. Cl.
*A61K 36/8945* (2006.01)
*A61K 36/288* (2006.01)
*A61K 36/538* (2006.01)

(52) U.S. Cl.
CPC ........ *A61K 36/8945* (2013.01); *A61K 36/288* (2013.01); *A61K 36/538* (2013.01); *A61K 2236/333* (2013.01)

(58) Field of Classification Search
None
See application file for complete search history.

(56) References Cited

U.S. PATENT DOCUMENTS

| | | | |
|---|---|---|---|
| 8,173,711 B2 | 5/2012 | Saito et al. | |
| 2010/0028318 A1 | 2/2010 | Saito et al. | |

FOREIGN PATENT DOCUMENTS

| | | | |
|---|---|---|---|
| CN | 1711878 A | 12/2005 | |
| CN | 10488657 A | 9/2015 | |
| CN | 105412030 A | 3/2016 | |
| CN | 105748979 A | 7/2016 | |
| CN | 105963648 A | 9/2016 | |
| EP | 1498130 A1 | 1/2005 | |
| KR | 10-2001-0068273 A | 7/2001 | |
| KR | 10-2004-0000046 A | 1/2004 | |
| KR | 10-2010-0084926 A | 7/2010 | |
| KR | 10-2017-0120797 A | 11/2017 | |
| WO | WO-2017023000 A1 | 2/2017 | |

OTHER PUBLICATIONS

CN105412030A, machine translation by Google. (Year: 2016).*
CN105963648A, machine translation by Google. (Year: 2016).*
ESR of EP Patent Application No. 19768358.4 dated Mar. 24, 2021.
Zhao, Y., et al.; "The effects of Chinese Yam-Epimedium mixture on respiratory function and quality of life in patients with chronic obstructive pulmonary disease", Journal of Traditional Chinese Medicine, 2012, 32(2), pp. 203-207.
Lee, W., et al.; "Botanical formulation, TADIOS, alleviates lipopolysaccharide (LPS)-Induced acute lung injury in mice via modulation of the Mrf2-HO-1 signaling pathway", Journal of Ethnopharmacology, 270, 2021, 113795.
International Search Report from corresponding PCT Application No. PCT/KR2019/003056, dated Jul. 12, 2019, with English translation.
OA of JP Patent Application No. 2020-549806 dated Aug. 17, 2021.
CN Patent Application No. 201980019847.5 dated Sep. 1, 2021.
Shi Siwei edited, "Health Maintenance with Flowers—Flower Medicated Diets and Prescriptions", Shanghai Scientific and Technological Literature Press, Jan. 2005, p. 301.
Huang Lingsu edited, "Extant Herbal Medicine Prescriptions—Removal of All Diseases", Beijing United Publishing Co., Ltd., Mar. 2015, p. 164.

* cited by examiner

*Primary Examiner* — Michael Barker
(74) *Attorney, Agent, or Firm* — Harness, Dickey & Pierce, P.L.C.

(57) ABSTRACT

The present disclosure relates to a pharmaceutical composition for preventing or treating respiratory diseases and a food composition for preventing or relieving respiratory diseases comprising a mixed extract of Dioscoreae Rhizoma, Taraxaci Herba and Schizonepetae Spica as an active ingredient. A composition comprising a mixed extract of Dioscoreae Rhizoma, Taraxaci Herba and Schizonepetae Spica of the present disclosure has an advantage of preventing respiratory diseases and relieving the symptoms of respiratory diseases, restores damages in the lung tissue and has efficacy for inhibiting inflammation, oxidative stress and ageing reactions induced by fine dust. More particularly, the composition of the present disclosure increases the expression of a telomerase which extends the length of a telomere, and thus is expected to fundamentally treat degenerative respiratory diseases induced by fine dust unlike existing symptom alleviating agents.

4 Claims, 14 Drawing Sheets

Specification includes a Sequence Listing.

CRUDE DRUG COMPOSITION FOR PREVENTING OR TREATING RESPIRATORY DISEASES

CROSS-REFERENCE TO RELATED APPLICATIONS

This application is a national phase application of PCT Application No. PCT/KR2019/003056, filed on Mar. 15, 2019, which claims the benefit of and priority to Korean Patent Application No. 10-2019-0028956, filed Mar. 13, 2019 and Korean Patent Application No. 10-2018-0031150, filed Mar. 16, 2018. The entire disclosures of the applications identified in this paragraph are incorporated herein by references.

FIELD

The present disclosure relates to an herbal medicine composition for prevention or treatment of a respiratory disease and, specifically, to a composition for prevention, treatment, or alleviation of a respiratory disease, the composition comprising extracts of Dioscoreae Rhizoma, Taraxaci Herba, and Schizonepetae Spica.

BACKGROUND

Respiratory diseases are diseases in connection with the lungs and airways, and may be mainly caused by lowered immunity, inflammatory actions, bacterial or viral infections, inhalation of harmful particles due to fine dust or smoking, aging, and the like. Representative respiratory diseases include pneumonia, rhinitis, asthma, bronchitis, tuberculosis, chronic obstructive pulmonary disease (COPD), and the like. Particularly, chronic obstructive pulmonary disease patients are recently increasing due to an increase in fine dust, smoking, and the like. Chronic obstructive pulmonary disease is also called emphysema or chronic bronchitis.

Medicines for such respiratory diseases are being developed mainly targeting anti-inflammatory actions or airway dilation effects. Examples of respiratory disease medicines showing anti-inflammatory and airway dilation effects are glucocorticoid steroid drugs, beta$_2$-adrenergic receptor agonists, leukotriene receptor antagonists, and phosphodiesterase-4 inhibitors (PDE4 inhibitors). However, the therapeutic purposes of these existing respiratory disease medicines are restricted to allergic asthma in infants or children and chronic obstructive pulmonary disease (COPD) in smokers. Moreover, most of the medicines are used for only a purpose of relieving symptoms, and have a limitation in that the medicines fail to delay or stop the progression of respiratory diseases through the removal of fundamental causes of the respiratory diseases. Since most of respiratory diseases have complicated causes and symptoms, existing medicines using a single component or a single therapeutic mechanism cannot obtain suitable therapy. Accordingly, there is an urgent need to develop a novel medicine for preventing and treating a respiratory disease more diversely and complexly.

SUMMARY

Technical Problem

The present inventors have made research efforts for developing a respiratory disease medicine having a novel therapeutic mechanism to overcome the limitations of the existing respiratory disease medicines described above. As a result, the present inventors verified that a complex herbal medicine extract (mixed extract) of Dioscoreae Rhizoma, Taraxaci Herba, and Schizonepetae Spica has effects of inhibiting inflammation, oxidative stress, and aging caused by fine dust, as well as lung tissue damage, and thus have completed the present invention.

Accordingly, an aspect of the present disclosure is to provide a pharmaceutical composition for prevention or treatment of a respiratory disease, the pharmaceutical composition comprising: as an active ingredient, a mixed extract of Dioscoreae Rhizoma, Taraxaci Herba, and Schizonepetae Spica; and a pharmaceutically acceptable carrier.

Another aspect of the present disclosure is to provide a food composition for prevention or alleviation of a respiratory disease, the food composition comprising, as an active ingredient, a mixed extract of Dioscoreae Rhizoma, Taraxaci Herba, and Schizonepetae Spica.

Technical Solution

In accordance with an aspect of the present disclosure, there is provided a pharmaceutical composition for prevention or treatment of a respiratory disease, the pharmaceutical composition comprising: (a) as an active ingredient, a mixed extract of Dioscoreae Rhizoma, Taraxaci Herba, and Schizonepetae Spica; and (b) a pharmaceutically acceptable carrier.

Herein, Dioscoreae Rhizoma is a rhizome (stalk with roots) steamed and dried as it is after the main bark of *Dioscorea batatas* Decaisne or *Dioscorea japonica* Thunberg is removed. The raw material of this medicine originates in China, but is also grown naturally or cultured in Korea, Japan, and Taiwan. Dioscoreae Rhizoma is a cylindrical or uneven cylindrical rhizome. In general, the rhizomes are collected in autumn, peeled, and then dried in the shade before use.

Herein, Taraxaci Herba indicates a whole plant of *Taraxacum platycarpum* H. Dahlstedt, *Taraxacum officinale* Weber, *Taraxacum mongolicum* Handel-Mazzetti, or *Taraxacum coreanum* Nakai. Donguibogam describes that Taraxaci Herba shows good effects of releasing heat poisoning, suppressing pestilent lesions, loosening lumps, removing dietary poisoning, and eliminating indigestion.

Herein, Schizonepetae Spica is a floral axis (flower petal) of *Schizonepeta tenuifolia* Briquet. Schizonepetae Spica is a flower petal that has a thin and long barley ear shape, is 5-10 cm in length, and is purple-greenish brown to greenish brown. Small lip-like flowers and often calyx tubes having fruits are linked thereto. Small milky short furs can be also seen on the entirety of the stalks. Schizonepetae Spica is known to have warmth, non-toxicity, and spiciness.

The extracts of Dioscoreae Rhizoma, Taraxaci Herba, and Schizonepetae Spica used in the present disclosure may be purchased, or obtained by direct extraction from the herbal medicines. The extraction may be performed after the respective herbal medicines are cut or pulverized into proper sizes.

In a case where the extracts used in the composition of the present disclosure are obtained by direct extraction from the herbal medicines Dioscoreae Rhizoma, Taraxaci Herba, and Schizonepetae Spica, various extraction solvents, such as polar solvents or non-polar solvents, may be used.

Suitable polar solvents may include (i) water, (ii) a C1 to C6 lower alcohol (specifically, methanol, ethanol, propanol, butanol, n-propanol, iso-propanol, n-butanol, 1-pentanol, 2-butoxyethanol, or ethylene glycol), (iii) acetic acid, (iv) dimethyl-formamide (DMFO), and (v) dimethyl sulfoxide (DMSO). Suitable non-polar solvents include acetone, acetonitrile, ethyl acetate, methyl acetate, fluoroalkanes, pentane, hexane, 2,2,4-trimethylpentane, decane, cyclohexane, cyclopentane, diisobutylene, 1-pentene, 1-chlorobutane, 1-chloropentane, o-xylene, diisopropylether, 2-chloropropane, toluene, 1-chloropropane, chlorobenzene, benzene, diethyl ether, diethyl sulfide, chloroform, dichloromethane, 1,2-dichloroethane, aniline, diethyl amine, ether, carbon tetrachloride, and tetrahydrofuran (THF).

The amount of the extraction solvent may vary depending on the amounts of Dioscoreae Rhizoma, Taraxaci Herba, and Schizonepetae Spica to be subjected to extraction, and specifically, the extraction solvent has a volume 1-20 times, specifically, 5-15 times, more specifically, 5-12 times, or 7-12 times the weight of Dioscoreae Rhizoma, Taraxaci Herba, and Schizonepetae Spica, or a mixture thereof. Most specifically, the extraction solvent has a volume 10 times the weight of Dioscoreae Rhizoma, Taraxaci Herba, Schizonepetae Spica, or a mixture thereof.

The extraction temperature of the extracts of the present disclosure is not particularly limited, and the extraction temperature may be for example 0-120° C., and specifically, 15-95° C. In an embodiment of the present disclosure, the extraction temperature is room temperature.

The extraction time of the extracts of the present disclosure is not particularly limited, and the extraction time may be for example 1 hour to 10 days, specifically, 1-72 hours, 1-48 hours, 1-36 hours, 1-24 hours, 1-12 hours, 1-10 hours, or 1-6 hours. The extraction time may be more specifically, 2-72 hours, 2-48 hours, 2-36 hours, 2-24 hours, 2-12 hours, 2-10 hours, 2-6 hours, 3-72 hours, 3-48 hours, 3-36 hours, 3-24 hours, 3-12 hours, 3-10 hours, 5-48 hours, 5-36 hours, 5-24 hours, 5-12 hours, 5-10 hours, 6-12 hours, or 6-10 hours, and most specifically, 8 hours.

The extracts of the present disclosure may be extracted by a known natural substance extraction method. For example, the extraction may be carried out by cold extraction, hot-water extraction, ultrasonic extraction, reflux cooling extraction, or heating extraction, and specifically, cold extraction. The extraction may be repeated one to ten times, and more specifically two to seven times.

According to an embodiment of the present disclosure, the extracts of Dioscoreae Rhizoma, Taraxaci Herba, and Schizonepetae Spica used in the present disclosure can be extracted with an organic solvent, water, or a mixed solvent thereof. Examples of the organic solvent include a C1 to C6 lower alcohol, petroleum ether, hexane, benzene, chloroform, methylene chloride, ether, ethyl acetate, and acetone.

The concentration of the organic solvents, such as a C1 to C6 lower alcohol, petroleum ether, hexane, benzene, chloroform, methylene chloride, ether, ethyl acetate, and acetone, may be 1-100% (v/v), specifically 10-100% (w/w), 20-100% (w/w), 30-100% (w/w), 40-100% (w/w), 50-100% (w/w), 60-100% (w/w), 70-100% (w/w), 80-100% (w/w), and more specifically 10-90% (w/w), 10-80% (w/w), 10-70% (w/w), 10-60% (w/w), 10-50% (w/w), 10-40% (w/w), or 10-30% (w/w), still more specifically 20-80% (w/w), 20-70% (w/w), 20-60% (w/w), 20-50% (w/w), 20-40% (w/w), or 20-30% (w/w), and most specifically 25% (w/w), but is not limited thereto.

According to still another embodiment of the present disclosure, the extracts of Dioscoreae Rhizoma, Taraxaci Herba, and Schizonepetae Spica of the present disclosure may be extracted with water, a C1 to C6 lower alcohol, or a mixed solvent thereof as described above, or may be, after extraction and concentration (under reduced pressure), further extracted or fractionated with an organic solvent selected from the group consisting of petroleum ether, hexane, benzene, chloroform, methylene chloride, ether, ethyl acetate, and acetone as described above.

Meanwhile, the mixed extract of the extracts of Dioscoreae Rhizoma, Taraxaci Herba, and Schizonepetae Spica used in the present disclosure may be prepared by mixing individual extracts of Dioscoreae Rhizoma, Taraxaci Herba, and Schizonepetae Spica, or may be prepared by treating a mixture of the herbal medicines Dioscoreae Rhizoma, Taraxaci Herba, and Schizonepetae Spica with an extraction solvent.

In the present disclosure, the extracts of Dioscoreae Rhizoma, Taraxaci Herba, and Schizonepetae Spica may be used in the form of a crude extract extracted by a solvent, and may be used through high-purity purification.

As used herein, the term "extract" has a meaning that is commonly used as a crude extract in the art as described above, and broadly, encompasses a fraction obtained by additionally fractionating the extract. In other words, the extracts of Dioscoreae Rhizoma, Taraxaci Herba, and Schizonepetae Spica include not only ones obtained by using the above-described extraction solvents but also ones obtained by additionally applying a purification procedure to the same. For example, the extracts of Dioscoreae Rhizoma, Taraxaci Herba, and Schizonepetae Spica of the present disclosure include fractions obtained through various purification methods that are additionally performed, such as a fraction obtained by passing the extracts through an ultra-filtration membrane with a predetermined molecular weight cut-off value and a fraction obtained by various types of chromatography (fabricated for separation depending on size, charge, hydrophobicity, or hydrophilicity). The extracts of Dioscoreae Rhizoma, Taraxaci Herba, and Schizonepetae Spica used in the present disclosure may be prepared in a powder type by additional procedures, such as distillation under reduced pressure and freeze-drying or spray drying.

According to a specific embodiment of the present disclosure, Dioscoreae Rhizoma, Taraxaci Herba, and Schizonepetae Spica are washed and dried, and then mixed at a predetermined weight ratio. Thereafter, the mixture is placed in an extraction solvent having a volume (ml) 1-20 times the weight (g) thereof, and then subjected to extraction while well stirred at 15-95° C. for 1-48 hours. Then, the extract was filtered, concentrated under reduced pressure at 50-65° C., and then freeze-dried, thereby obtaining a powder-type complex herbal medicine extract (mixed extract).

According to another embodiment of the present disclosure, Dioscoreae Rhizoma, Taraxaci Herba, and Schizonepetae Spica are separately placed in an extraction solvent having a volume (ml) 1-20 times the weight (g) thereof, and then subjected to extraction while well stirred at 15-95° C. for 1-48 hours. Then, each extract is filtered, concentrated under reduced pressure at 50-65° C., and then freeze-dried, thereby obtaining a powder-type herbal medicine extract. Thereafter, the respective herbal medicine extracts are mixed at a predetermined weight ratio, thereby obtaining a powder-type complex herbal medicine extract (mixed extract).

According to a particular embodiment of the present disclosure, Dioscoreae Rhizoma, Taraxaci Herba, and Schizonepetae Spica are mixed at a weight ratio of 1:1:1, and then ethanol having a volume 10 times the weight is added thereto, followed by extraction at room temperature for 8 hours. The extract is concentrated under reduced pressure at 50-65° C., and then the concentrate is freeze-dried, thereby obtaining a complex herbal medicine extract of Dioscoreae Rhizoma, Taraxaci Herba, and Schizonepetae *Spica*.

The mixed extract of three kinds, Dioscoreae Rhizoma, Taraxaci Herba, and Schizonepetae Spica used in the present disclosure may contain herbal medicine extracts of Dioscoreae Rhizoma, Taraxaci Herba, and Schizonepetae Spica at a mixing weight ratio of 1-10:1-10:1-10, 1:1-10:1-10, 1-10:1:1-10, 1-10:1-10:1, 1:1:1-10, 1:1-10:1, or 1-10:1:1, at a mixing weight ratio of 1-5:1-5:1-5, 1:1-5:1-5, 1-5:1:1-5, 1-5:1-5:1, 1:1:1-5, 1:1-5:1, or 1-5:1:1, at a mixing weight ratio of 1-4:1-4:1-4, 1:1-4:1-4, 1-4:1:1-4, 1-4:1-4:1, 1:1:1-4, 1:1-4:1, or 1-4:1:1, or at a mixing weight ratio of 1-3:1-3:1-3, 1:1-3:1-3, 1-3:1:1-3, 1-3:1-3:1, 1:1:1-3, 1:1-3:1, 1-3:1:1, or 1:1:1.

The mixing ratio of the herbal medicine ingredients described herein is calculated on the basis of the weight of solvent-removed solids (in a case of a mixture of herbal medicine extracts) or the weight of herbal medicines per se (in a case of an extract of mixed herbal medicines).

As used herein, the term "to" or "-" between two numerical values refers to an interval between the numerical values including numerical values described before and after the term.

The composition of the present disclosure may be prepared into a pharmaceutical composition.

According to a specific embodiment of the present disclosure, the composition of the present disclosure is a pharmaceutical composition comprising: (a) as an active ingredient, the above-described mixed extract of Dioscoreae Rhizoma, Taraxaci Herba, and Schizonepetae Spica; and (b) a pharmaceutically acceptable carrier.

As used herein, the term "pharmaceutical effective amount" refers to an amount sufficient to attain efficacy of the above-described mixed extract of Dioscoreae Rhizoma, Taraxaci Herba, and Schizonepetae Spica to treat or prevent a respiratory disease. The present disclosure is directed to a composition comprising extracts extracted from the natural plant materials, Dioscoreae Rhizoma, Taraxaci Herba, and Schizonepetae Spica, and even the administration of an excess of the composition causes no side effects in the human body, and thus a person skilled in the art could select and implement the upper limit of the amount of the extracts contained in the composition of the present disclosure.

As used herein, the term "respiratory disease" includes a respiratory disease selected from the group consisting of a cold, rhinitis, pharyngitis, laryngitis, pharyngolaryngitis, acute or chronic pneumonia, acute or chronic bronchitis, asthma, and chronic obstructive pulmonary disease, but is not limited thereto.

As validated in the following examples, the administration of the complex herbal medicine extract (mixed extract) of Dioscoreae Rhizoma, Taraxaci Herba, and Schizonepetae Spica shows an effect of significantly reducing lung tissue damage in emphysema mouse models.

In addition, the complex herbal medicine extract of the present disclosure significantly inhibits reactive oxygen species generation, apoptosis, and aging in pulmonary epithelial cell lines, induced by fine dust, and dose-dependently increases the expression degree of telomerase that extends the length of telomere.

In addition, the complex herbal medicine extract of the present disclosure shows an excellent anti-inflammatory effect by inhibiting NO production of the mouse macrophage cell line treated with LPS.

The complex herbal medicine extract of the present disclosure also shows an excellent anti-inflammatory effect by inhibiting the expression of the inflammatory factors (IL-6, IL-1β, and iNOS) expressed in the mouse macrophage cell line treated with LPS.

The complex herbal medicine extract of the present disclosure also shows an excellent antioxidative effect by increasing the expression of the antioxidative factor HO-1 in the mouse macrophage cell line treated with LPS, and shows an excellent antioxidative effect even in various ratio ranges of herbal medicines even when the cell lines were treated with complex herbal medicine extracts comprising herbal medicines at various ratios.

The complex herbal medicine extract of the present disclosure also shows an excellent anti-inflammatory effect by inhibiting the expression of an anti-inflammatory factor (iNOS) even when the extract is extracted with an extraction solvent (ethanol) at various concentrations, and shows an excellent antioxidative effect by increasing the expression of the antioxidative factor HO-1 even when the concentrations and kinds of the extraction solvent are different.

As well, the complex herbal medicine extract of the present disclosure, compared with a single herbal medicine extract, significantly inhibits the expression of inflammatory factors (IL-6, IL-1β, and TNF-α) in the lung tissue of the pulmonary inflammation models induced by LPS, thereby showing a synergistic effect in an anti-inflammatory effect compared with a single herbal medicine extract.

The above results of the examples indicate that the composition comprising the complex herbal medicine extract of the present disclosure can be used in the prevention, alleviation, or treatment of a respiratory disease, such as pneumonia, bronchitis, chronic obstructive pulmonary disease, or asthma, caused by inflammation and aging, and can be used as an alternative for a conventional respiratory disease medicine.

In cases where the composition of the present disclosure is prepared into a pharmaceutical composition, the pharmaceutical composition of the present disclosure may contain a pharmaceutically acceptable carrier. The pharmaceutically acceptable carrier is normally used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, mineral oil, and the like. The pharmaceutical composition of the present disclosure may further contain, in addition to the above ingredients, a lubricant, a humectant, a sweetener, a flavoring agent, an emulsifier, a suspending agent, a preservative, and the like. Suitable pharmaceutically acceptable carriers and preparations are described in detail in Remington's Pharmaceutical Sciences (19th ed., 1995).

The pharmaceutical composition of the present disclosure may be administered orally or parenterally, and examples of parenteral administration may include intravenous administration, subcutaneous administration, intradermal administration, intramuscular administration, intranasal administration, mucosal administration, intradural administration, intraperitoneal administration, intraocular administration, and the like, and specifically, the pharmaceutical composition of the present disclosure may be administered orally.

The suitable dose of the pharmaceutical composition of the present disclosure varies depending on factors, such as a formulating method, a manner of administration, patient's age, body weight, gender, morbidity, and food, a time of administration, a route of administration, an excretion rate, and response sensitivity. The ordinarily skilled practitioners can easily determine and prescribe the dose that is effective for the desired treatment or prevention. According to a specific embodiment of the present disclosure, the daily dose of the pharmaceutical composition of the present disclosure is 0.001-1,000 mg/kg. The daily dose of the pharmaceutical composition of the present disclosure may be for example 0.1-1000 mg/kg, 0.1-900 mg/kg, 0.1-800 mg/kg, 0.1-700 mg/kg, 0.1-600 mg/kg, 0.1-500 mg/kg, 0.1-400 mg/kg, 0.1-300 mg/kg, 0.1-200 mg/kg, 0.1-100 mg/kg, 0.1-50 mg/kg, 0.1-30 mg/kg, 0.1-20 mg/kg, 0.1-10 mg/kg, 0.1-7 mg/kg, or 0.1-5 mg/kg, and may be 1-1000 mg/kg, 1-900 mg/kg, 1-800 mg/kg, 1-700 mg/kg, 1-600 mg/kg, 1-500 mg/kg, 1-400 mg/kg, 1-300 mg/kg, 1-200 mg/kg, 1-100 mg/kg, 1-50 mg/kg, 1-30 mg/kg, 1-20 mg/kg, 1-10 mg/kg, 1-7 mg/kg, or 1-5 mg/kg, and more specifically may be 1, 2, 3, 4, 5, 6, 7, 8, 9, or 10 mg/kg. In another embodiment, the daily dose of the pharmaceutical composition of the present disclosure may be for example 100-900 mg/kg, 100-800 mg/kg, 100-700 mg/kg, 100-600 mg/kg, 100-500 mg/kg, 100-400 mg/kg, 100-300 mg/kg, or 100-200 mg/kg, may be 200-900 mg/kg, 200-800 mg/kg, 200-700 mg/kg, 200-600 mg/kg, 200-500 mg/kg, 200-400 mg/kg, or 200-300 mg/kg, may be 300-900 mg/kg, 300-800 mg/kg, 300-700 mg/kg, 300-600 mg/kg, 300-500 mg/kg, or 300-400 mg/kg, and may be 400-900 mg/kg, 400-800 mg/kg, 400-700 mg/kg, 400-600 mg/kg, or 400-500 mg/kg, and more specifically, 100 mg/kg, 200 mg/kg, 300 mg/kg, 400 mg/kg, 500 mg/kg, 600 mg/kg, 700 mg/kg, 800 mg/kg, 900 mg/kg, or 1000 mg/kg, but is not limited thereto.

The pharmaceutical composition of the present disclosure may be formulated into a unit dosage form or may be prepared in a multi-dose container by using a pharmaceutically acceptable carrier and/or excipient according to a method that can be easily implemented by a person having an ordinary skill in the art to which the present disclosure pertains. The formulation may be a solution in an oily or aqueous medium, a suspension, an emulsion, an extract, a powder, granules, a tablet, or a capsule, and may further contain a dispersant or a stabilizer.

The pharmaceutical composition of the present disclosure may be administered in combination with a known compound or pharmaceutical composition having effects of preventing and treating a respiratory disease or respiratory disease-related symptoms.

According to another aspect of the present disclosure, there is provided a food composition for prevention or alleviation of a respiratory disease, the food composition comprising, as an active ingredient, a mixed extract of Dioscoreae Rhizoma, Taraxaci Herba, and Schizonepetae Spica. The food composition may be used as a health functional food or may be added to various types of foods.

The present disclosure also provides a health functional food comprising the food composition. The health functional food may be drinks, meats, chocolates, foods, confectionery, pizzas, instant noodles, other noodles, gums, ice creams, alcohol drinks, vitamin complexes, and health supplement foods.

The content of the mixed extract of the present disclosure contained in the food composition may be appropriately controlled according to the form of food, the desired use, or the like, and is not particularly limited thereto. For example, the content of the mixed extract may be 0.001-30 wt % or 0.01-20 wt % of the entire food weight, and the health food composition may be 0.001-15 g, 0.02-10 g, or 0.3-1 g on the basis of 100 ml thereof, but is not limited thereto.

The composition comprising a mixed extract of Dioscoreae Rhizoma, Taraxaci Herba, and Schizonepetae Spica of the present disclosure, when prepared into a food composition, may contain ingredients that are ordinarily added in the manufacture of foods as well as the extract as an active ingredient. The added ingredients include, for example, a protein, a carbohydrate, a fat, a nutrient, a seasoning, and a flavoring agent. Examples of the foregoing carbohydrate may include typical sugars (monosaccharides, such as glucose and fructose; disaccharides, such as maltose, sucrose, and oligosaccharides; and polysaccharides, such as dextrin and cyclodextrin) and sugar alcohols, such as xylitol, sorbitol, and erythritol. Examples of the flavoring agent may include natural flavoring agents (thaumatin, and stevia extract (e.g., rebaudioside A, glycyrrhizin, etc.)) and synthetic flavoring agents (saccharin, aspartame, etc.). For example, the food composition of the present disclosure, when is prepared into a drink, may further contain citric acid, liquefied fructose, sugar, glucose, acetic acid, malic acid, fruit juice, an Eucommia ulmoides extract, a jujube extract, and a licorice extract, in addition to the extract of the present disclosure.

Since the food composition for prevention or alleviation of a respiratory disease of the present disclosure contains, as an active ingredient, a mixed extract of Dioscoreae Rhizoma, Taraxaci Herba, and Schizonepetae Spica in the same manner as "the pharmaceutical composition for prevention or treatment of a respiratory disease" as described above, a description of overlapping contents therebetween is omitted to avoid excessive redundancy of the present specification.

According to still another aspect of the present disclosure, there is provided a method for prevention or treatment of a respiratory disease, the method including administering, to a subject, the pharmaceutical composition comprising, as an active ingredient, the above-described mixed extract of Dioscoreae Rhizoma, Taraxaci Herba, and Schizonepetae Spica of the present disclosure.

According to another aspect of the present disclosure, there is provided a method for prevention or alleviation of a respiratory disease, the method including administering, to a subject, the food composition comprising, as an active ingredient, the above-described mixed extract of Dioscoreae Rhizoma, Taraxaci Herba, and Schizonepetae Spica of the present disclosure.

The respiratory disease, which is the target disease of the treatment method or alleviation method of the present disclosure, is the same as defined in relation to the respiratory disease, which is the target disease to be treated with the pharmaceutical composition.

As used herein, the term "administration" or "administer" refers to the direct administration of a therapeutically or amelioratively effective amount of the composition of the present disclosure to a subject (i.e., an individual) undergoing a respiratory disease, thereby forming the same amount thereof in the body of the subject.

The term "therapeutically effective amount" of the composition refers to the content of the composition, which is sufficient to provide a therapeutic or preventive effect to a subject to which composition is administered, and thus the term has a meaning encompassing "prophylactically effective amount." As used herein, the term "subject" is a mammal including a human, a mouse, a rat, a guinea pig, a dog, a cat, a horse, a cow, a pig, a monkey, a chimpanzee, a baboon, or a rhesus monkey. Most specifically, the subject of the present disclosure is a human.

Since the method for prevention, alleviation, or treatment of a respiratory disease of the present disclosure includes administering the pharmaceutical composition for prevention or treatment or the food composition for prevention or alleviation of a respiratory disease according to an aspect of the present disclosure, a description of overlapping contents therebetween is omitted to avoid excessive redundancy of the present specification.

Advantageous Effects

Features and advantages of the present disclosure are summarized as follows.

(a) The present disclosure relates to a pharmaceutical composition for prevention or treatment of a respiratory disease and a food composition for prevention or alleviation of a respiratory disease, each of the compositions comprising a mixed extract of Dioscoreae Rhizoma, Taraxaci Herba, and Schizonepetae Spica.

(b) The composition comprising a mixed extract of Dioscoreae Rhizoma, Taraxaci Herba, and Schizonepetae Spica of the present disclosure has effects of preventing a respiratory disease and relieving symptoms thereof, and has effects of restoring lung tissue damage and inhibiting inflammation, oxidative stress, and aging induced by fine dust. Especially, the composition of the present disclosure is expected to be able to fundamentally treat a degenerative respiratory disease induced by fine dust, unlike a conventional symptom reliever, by increasing the expression of telomerase that extends the length of telomeres.

DETAILED DESCRIPTION

Figure 1:
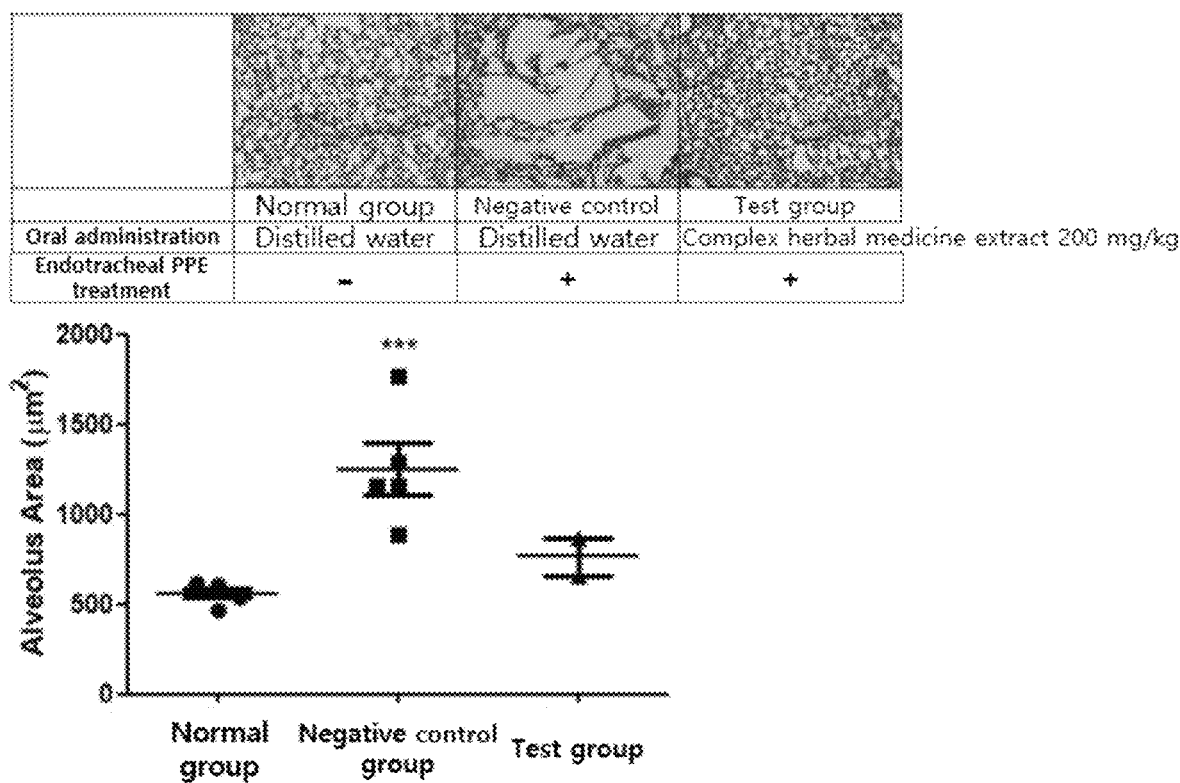
FIG. 1 shows the microscopic observation of lung tissues of PPE-induced emphysema mouse models, in order to investigate the lung tissue damage inhibitory effect of the complex herbal medicine extract of the present disclosure.

Hereinafter, the present disclosure will be described in more detail with reference to examples. These examples are only for illustrating the present disclosure more specifically, and it would be apparent to those skilled in the art that the scope of the present disclosure is not limited by these examples according to the gist of the present disclosure.

EXAMPLES

Throughout the present specification, the "%" used to express the concentration of a specific material, unless otherwise particularly stated, refers to (wt/wt) % for solid/solid, (wt/vol) % for solid/liquid, and (vol/vol) % for liquid/liquid.

Preparative Examples

Preparative Example 1: Preparation of Complex Herbal Medicine Extract (Mixed Extract)

Washed and dried Dioscoreae Rhizoma, Taraxaci Herba, and Schizonepetae Spica were used in tests. The herbal medicines Dioscoreae Rhizoma, Taraxaci Herba, and Schizonepetae Spica were mixed at a weight ratio of 1:1:1 to a total of 60 g, and 25% (v/v) ethanol aqueous solution having a volume 10 times the weight was added thereto, followed by extraction while well stirring at room temperature for 8 hours. The extract was filtered, concentrated under reduced pressure at 50-65° C., and then freeze-dried, thereby obtaining a powder-type complex herbal medicine extract (mixed extract). The yield was about 12-13%.

Preparative Example 2: Preparation of Complex Herbal Medicine Extract (Mixed Extract) According to Mixing Ratio of Herbal Medicines Washed and dried Dioscoreae Rhizoma, Taraxaci Herba, and Schizonepetae Spica were used in tests. The herbal medicines Dioscoreae Rhizoma, Taraxaci Herba, and Schizonepetae Spica were mixed at weight ratios shown in Table 1 to a total of 30 g, and 25% (v/v) ethanol aqueous solution having a volume 10 times the weight was added thereto, followed by extraction while well stirring at room temperature for 8 hours. Each of the extracts was filtered, concentrated under reduced pressure at 50-65° C., and then freeze-dried, thereby obtaining a total of seven types of complex herbal medicine extract powders. The yields thereof are shown in Table 1.

TABLE 1

| Classification | Dioscoreae Rhizoma | Taraxaci Herba | Schizonepetae Spica | Yield (%) |
|---|---|---|---|---|
| Preparative Example 2-1 | 1 | 1 | 1 | 11.95 |
| Preparative Example 2-2 | 2 | 1 | 1 | 13.17 |
| Preparative Example 2-3 | 4 | 1 | 1 | 14.81 |
| Preparative Example 2-4 | 1 | 2 | 1 | 11.84 |
| Preparative Example 2-5 | 1 | 4 | 1 | 10.83 |
| Preparative Example 2-6 | 1 | 1 | 2 | 10.49 |
| Preparative Example 2-7 | 1 | 1 | 4 | 10.27 |

Preparative Example 3: Preparation of Complex Herbal Medicine Extracts (Mixed Extracts) According to Various Concentrations of Extraction Solvent (Ethanol)

Washed and dried Dioscoreae Rhizoma, Taraxaci Herba, and Schizonepetae Spica were used in tests. The herbal medicines Dioscoreae Rhizoma, Taraxaci Herba, and Schizonepetae Spica were mixed at the weight ratio (w/w) in Preparative Example 2-1 to a total of 30 g, and 25, 50, 70, and 90% ethanol aqueous solutions having a volume 10 times the weight were added thereto, followed by extraction while well stirring at room temperature for 8 hours. Each of the extracts was filtered, concentrated under reduced pressure at 50-65° C., and then freeze-dried, thereby obtaining a total of four types of complex herbal medicine extract powders. The yields thereof are shown in Table 2.

TABLE 2

| Classification | Ethanol aqueous solution concentration (%) | Yield (%) | Note |
|---|---|---|---|
| Preparative Example 3-1 | 25 | 12.37 | Same preparation method as in Preparative Example 2-1 |
| Preparative Example 3-2 | 50 | 13.71 | — |
| Preparative Example 3-3 | 70 | 9.84 | — |
| Preparative Example 3-4 | 90 | 5.23 | — |

Preparative Example 4: Preparation of Complex Herbal Medicine Extract (Mixed Extract) Through Hot-Water Extraction Washed and dried Dioscoreae Rhizoma, Taraxaci Herba, and Schizonepetae Spica were used in tests. The herbal medicines comprising Dioscoreae Rhizoma, Taraxaci Herba, and Schizonepetae Spica were mixed at the weight ratio (w/w) in Preparative Example 2-1 to a total of 30 g, and distilled water having a volume 10 times the weight was added thereto, followed by reflow extraction at a temperature of 90° C. for 3 hours. The extract was filtered, concentrated under reduced pressure at 50-65° C., and then freeze-dried, thereby obtaining a complex herbal medicine extract powder, and the yield thereof was about 13.30%.

Comparative Example 1: Preparation of Single-Herbal Medicine Extracts

Washed and dried Dioscoreae Rhizoma, Taraxaci Herba, and Schizonepetae Spica were used in tests. To 30 g of each of the herbal medicines Dioscoreae Rhizoma, Taraxaci Herba, and Schizonepetae Spica, 25% (v/v) ethanol aqueous solution having a volume 10 times the weight was added, followed by extraction while well stirring at room temperature for 8 hours. Each of the extracts was filtered, concentrated under reduced pressure at 50-65° C., and then freeze-dried, thereby obtaining a total of three types of single-herbal medicine extract powders. The yields thereof are shown in Table 3.

TABLE 3

| Classification | Kind of herbal medicine | Yield (%) |
|---|---|---|
| Comparative Example 1-1 | Dioscoreae Rhizoma | 19.86 |
| Comparative Example 1-2 | Taraxaci Herba | 12.52 |
| Comparative Example 1-3 | Schizonepetae Spica | 7.84 |

Test Examples

Test Example 1: Lung Tissue Damage Inhibitory Effect of Complex Herbal Medicine Extract in PPE-Induced Emphysema Mouse Models In order to investigate a lung tissue damage inhibitory effect of the complex herbal medicine extract of the present disclosure prepared in Preparative Example 1, the following test was carried out.

After 7-week-old male C57BL/6 mice (Raonbio, Korea) were acclimated for at least one week, the animals were classified into (1) a normal group, (2) a group with emphysema induction and complex herbal medicine extract administration (test group), and (3) a group with emphysema induction and distilled water administration (negative control group). For the induction of emphysema in the test group and the negative control group, 1 U of porcine pancreatic elastase (PPE, Millipore, USA) was administered as a single drop into the mouse trachea. For the normal group, phosphate buffered saline (PBS) was administered as a single drop into the mouse trachea.

For the test group, the complex herbal medicine extract dissolved in distilled water was orally administered once/day at a dose of 200 mg/kg for two weeks from one week before PPE administration. For the normal group and the negative control group, only distilled water was orally administered. After the last administration of the complex herbal medicine extract or distilled water, the mice were anesthetized with carbon dioxide and the lung tissue was extracted. The extracted lung tissue was fixed in formalin and subjected to hematoxylin and eosin staining (H&E staining). The images taken by observing the lung tissue with an optical microscope (×100) are shown in FIG. 1.

As shown in FIG. 1, as a result of inducing emphysema by PPE, the alveolar dilation and lung tissue damage in the negative control group significantly increased by about 2.2 times compared with the normal group. In addition, the lung tissue damage was inhibited in the test group with administration of the complex herbal medicine extract compared with the emphysema induction group (negative control group).

It could be therefore verified that the complex herbal medicine extract of the present disclosure showed a lung tissue damage inhibitory effect in the emphysema mouse models.

Test Example 2: Inhibitory Effect of Complex Herbal Medicine Extract on Fine Dust-Induced Reactive Oxygen Species Formation of Pulmonary Epithelial Cell Line In order to investigate a reactive oxygen species formation inhibitory effect of the complex herbal medicine extract of the present disclosure prepared in Preparative Example 1, the following test was carried out.

The human pulmonary endothelial cell line NCI-H292 cells (ATCC, USA) were incubated in an incubator of 5% $CO_2$ and 37° C. by using RPMI media (Corning, USA) comprising 10% fetal bovine serum (FBS). The cells were prepared on a 96-well plate at $1\times10^4$ cells per well, and stabilized for 24 hours. After the cells were stabilized, the cell supernatant was removed, and then the cells were treated with the complex herbal medicine extract in Preparative Example 1 at 100 µg/ml, followed by incubation for 1 hour. Then, the cells were further treated with 200 µg/ml fine dust (particulate matter 10, PM10, NIST, USA) (test group). The normal group was treated with neither the complex herbal medicine extract nor fine dust, and the negative control group was treated with only fine dust. After 3 hours, the amount of reactive oxygen species formed in the cells was investigated by using DCF-DA analysis (Sigma Aldrich, USA).

Figure 2:
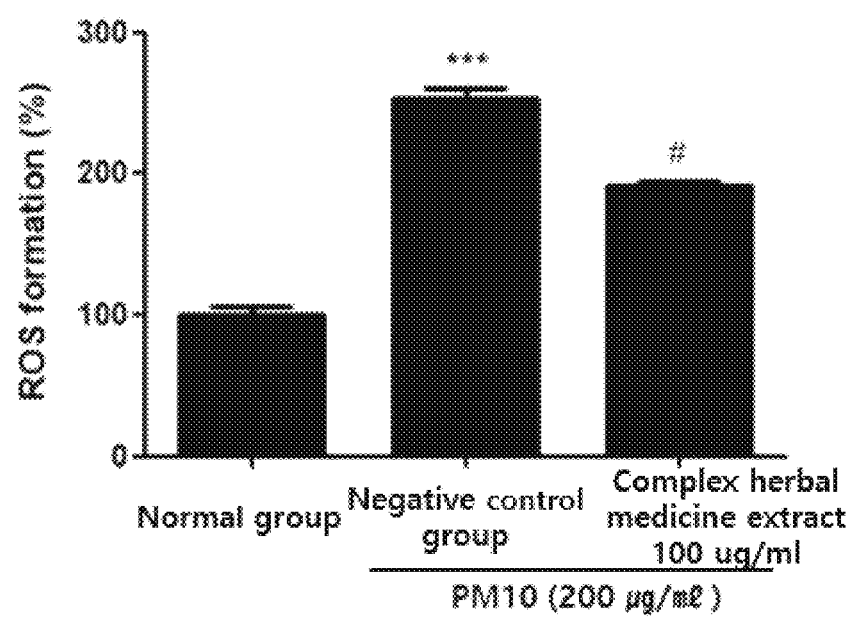
FIG. 2 is a graph comparing the degrees of reactive oxygen species (ROS) formation in the pulmonary endothelial cell line, induced by fine dust, in order to investigate the ROS formation inhibitory effect of the complex herbal medicine extract of the present disclosure.

As shown in FIG. 2, the reactive oxygen species was increased by about 125% in the group with fine dust induction (negative control group) compared with the normal group, and such reactive oxygen species was inhibited by about 61% through the complex herbal medicine extract. It can be therefore seen that the complex herbal medicine extract of the present disclosure showed an excellent antioxidative effect.

Test Example 3: Inhibitory Effect of Complex Herbal Medicine Extract on Fine Dust-Induced Apoptosis As in Test Example 2, NCI-H292 cells were prepared on a 96-well plate at $1\times10^4$ cells per well, and stabilized. After 24 hours, the cell supernatant was removed, and then the cells were treated with the complex herbal medicine extract in Preparative Example 1 at concentrations of 100, 200, 400, and 800 mg/mL. After 1 hour, the cells were further treated with 50 µg/mL fine dust (PM 10). The normal group was treated with neither the complex herbal medicine extract nor fine dust, and the negative control group was treated with only fine dust. After 24 hours, cell viability was investigated through the WST-1 test (Younginfrontier, Korea).

Figure 3:
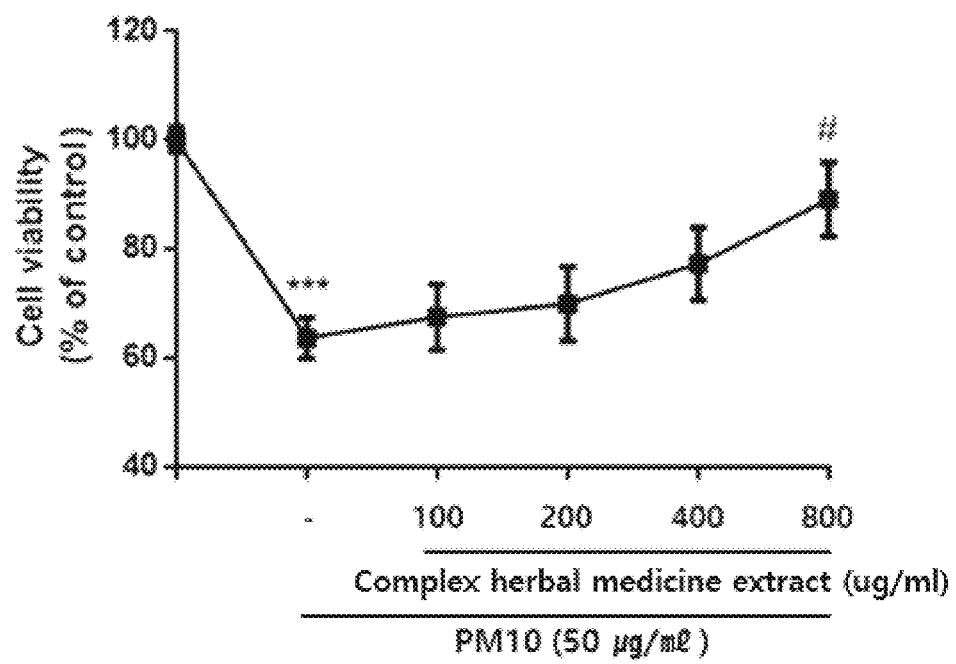
FIG. 3 is a graph comparing cell viability according to the concentrations (100, 200, 400, and 800 μg/ml) of the complex herbal medicine extract in the pulmonary endothelial cell line treated with fine dust, in order to investigate the apoptosis inhibitory effect of the complex herbal medicine extract of the present disclosure.

As shown in FIG. 3, as a result of treating the pulmonary epithelial cell line with fine dust, cell viability was about 63.6% compared with the normal group by apoptosis (negative control group). Whereas, the test groups with the treatment of the complex herbal medicine extract at concentrations of 100, 200, 400, and 800 µg/mL showed cell viability of 67.5%, 69.9%, 77.2%, and 89%, respectively, indicating that apoptosis was inhibited in a dose-dependent manner. It can be therefore seen that the complex herbal medicine extract of the present disclosure showed an excellent apoptosis inhibitory effect.

Test Example 4: Anti-Aging Effect of Complex Herbal Medicine Extract on Fine Dust-Induced Cell Aging of Pulmonary Epithelial Cell Line As in Test Example 2, NCI-H292 cells were prepared on a 96-well plate at $1\times10^4$ cells per well, and stabilized. After 24 hours, the cell supernatant was removed, and then the cells were treated with the complex herbal medicine extract in Preparative Example 1 at a concentration of 200 µg/Ml. After 1 hour, the cells were further treated with 50 µg/mL fine dust (PM 10). The normal group was treated with neither the complex herbal medicine extract nor fine dust, and the negative control group was treated with only fine dust. After five days, the cells were fixed in formalin, and then the degree of cell aging was investigated through senescence beta-galactosidase staining.

Figure 4:
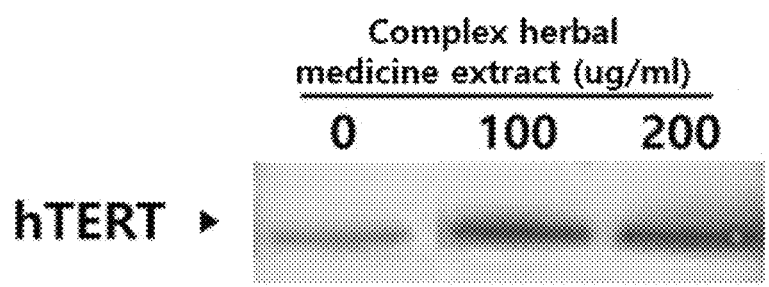
FIG. 4 shows the results of senescence beta-galactosidase staining after the treatment of the pulmonary endothelial cell line with fine dust, in order to investigate the anti-aging effect of the complex herbal medicine extract of the present disclosure.

As shown in FIG. 4, cell aging caused by fine dust treatment was significantly reduced in the test group treated with the complex herbal medicine extract compared with the negative control group. It can be therefore seen that the complex herbal medicine extract of the present disclosure showed an excellent anti-aging effect.

Test Example 5: Telomerase Expression Increasing Effect of Complex Herbal Medicine Extract in Pulmonary Endothelial Cell Line (Anti-Aging Effect)

NCI-H292 cells were prepared on a 100 pi (φ) plate at $1\times10^6$ cells and stabilized. After 24 hours, the cells were treated with the complex herbal medicine extract in Preparative Example 1 at concentrations of 100 and 200 µg/ml. After 24 hours, the cells were collected and proteins were extracted, and then western blotting was performed using an antibody (ab32020, Abcam, USA) for human telomerase reverse transcriptase (hTERT), which is a catalytic small unit of telomerase.

Figure 5:
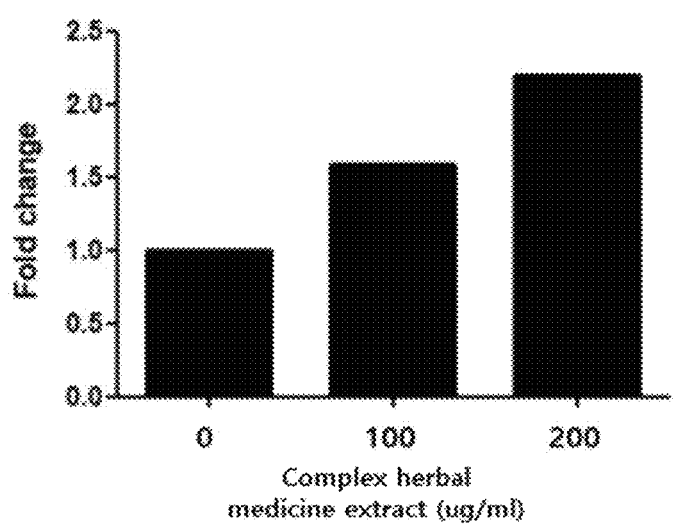
FIG. 5 shows the western blot results of comparing the expression degrees of telomerase according to the concentrations (100 and 200 μg/ml) of the complex herbal medicine extract in pulmonary endothelial cell lines, in order to investigate the anti-aging effect of the complex herbal medicine extract of the present disclosure.

As shown in FIG. 5, the pulmonary endothelial cell line was treated with the complex herbal medicine extract at concentrations of 100 and 200 µg/ml, and as a result, the expression of hTERT dose-dependently increased to 1.6 times and 2.2 times, respectively, compared with the non-treatment group (control group). It can be therefore seen that the complex herbal medicine extract of the present disclosure showed an excellent anti-aging effect.

Test Example 6: Inhibitory Effect (Anti-Inflammatory Effect) of Complex Herbal Medicine Extract on LPS-Induced Nitric Oxide (NO) Production in Macrophage Cell Line The mouse macrophage cell line Raw 264.7 cells (ATCC, USA) were incubated in the incubator of 5% $CO_2$ and 37° C.

by using RPMI media (Invitrogen, USA) comprising 10% fetal bovine serum (FBS). The cells were prepared on a 24-well plate at 2.5×10⁵ cells per well, and stabilized. After 24 hours, the cell supernatant was removed, and then the cells were treated with the complex herbal medicine extract in Preparative Example 1 at concentrations of 0.5, 1, 2, and 4 mg/mL. After 1 hour, the cells were further treated with 100 ng/mL LPS. After 24 hours, the cell supernatant was collected and subjected to Griess test for measuring the change in NO production, and the concentration of NO was calculated using the standard curve according to the concentration of sodium nitrite (NaNO₂) (FIG. 6).

Figure 6:
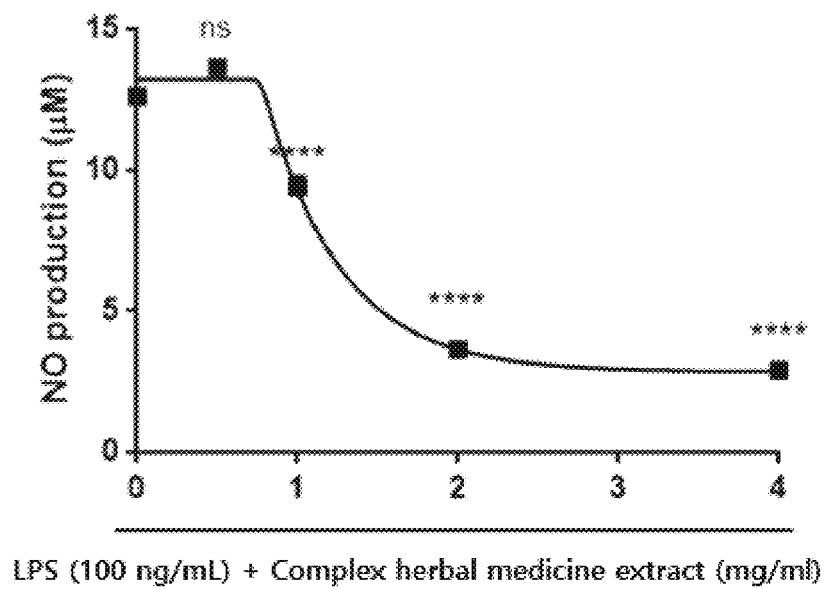
FIG. 6 is a graph comparing the degrees of nitric oxide (NO) production according to the treatment concentrations (0.5, 1, 2, 4 mg/ml) of the complex herbal medicine extract in mouse macrophage cell line treated with LPS, in order to investigate the anti-inflammatory effect of the complex herbal medicine extract of the present disclosure.

As shown in FIG. 6, the production of NO, which is an inflammatory factor, increased to a level of 12 μM by LPS treatment in macrophages (negative control group). In the test group treated with the complex herbal medicine extract at concentrations of 0.5, 1, 2, and 4 mg/ml together with LPS, the NO concentrations were 13.6, 9.4, 3.6, and 3 μM, respectively, showing a concentration-dependent reduction. It can be therefore seen that the complex herbal medicine extract of the present disclosure showed an excellent anti-inflammatory effect.

Figure 7A:
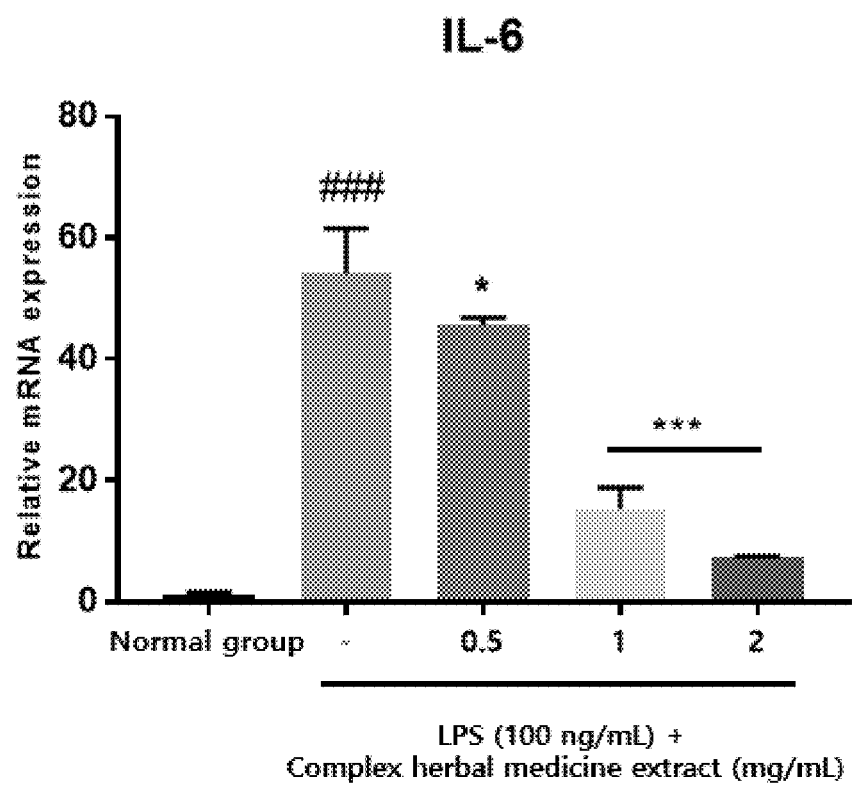
FIGS. 7A, 7B and 7C are graphs showing the expression inhibitory effect of the complex herbal medicine extract of the present disclosure on the expression of the inflammatory factors (IL-6, IL-1β, and iNOS) in mouse macrophage cell line treated with LPS, in order to investigate the anti-inflammatory effect of the complex herbal medicine extract of the present disclosure.
Figure 7B:
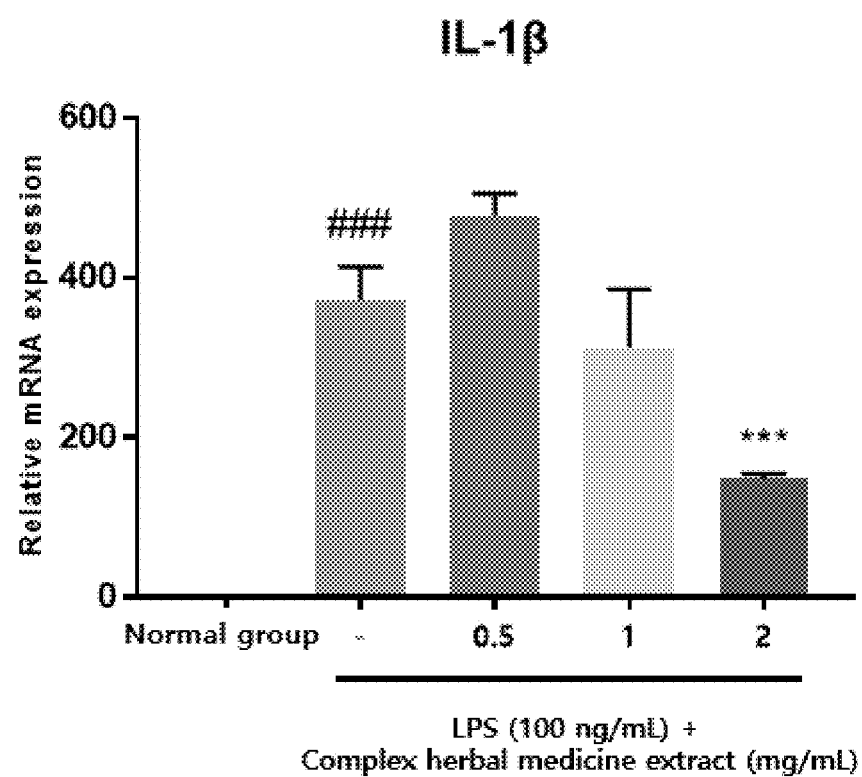
Figure 7C:
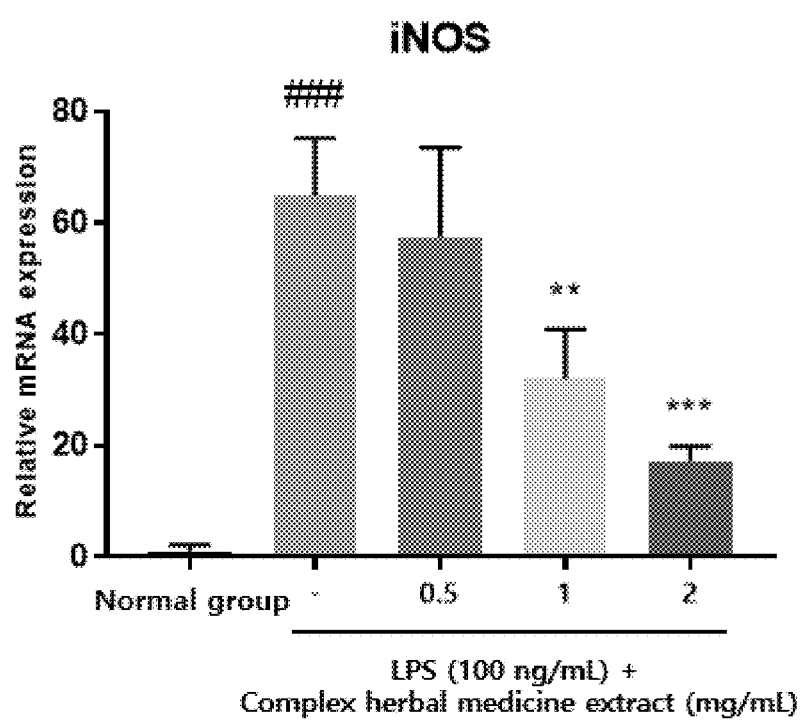

Test Example 7: Inhibitory Effect (Anti-Inflammatory Effect) of Complex Herbal Medicine Extract on LPS-Induced Inflammatory Factor Expression in Macrophage Cell Line The mouse macrophage cell line Raw 264.7 cells (ATCC, USA) were incubated in an incubator of 5% CO₂ and 37° C. by using RPMI media (Invitrogen, USA) comprising 10% fetal bovine serum (FBS). The cells were prepared on a 24-well plate at 2.5×10⁵ cells per well, and stabilized. After 24 hours, the cell supernatant was removed, and then the cells were treated with 100 ng/mL LPS (Sigma, US) and the complex herbal medicine extract in Preparative Example 1 at concentrations of 0.5, 1, and 2 mg/mL. After 24 hours, the cell supernatant was removed, and then RNA was separated from the cells by using TRIzol (Invitrogen, USA). Thereafter, cDNA obtained through RT-PCR was used to perform qPCR using primers specific to the inflammatory factors IL-6, IL-1β, and iNOS and the SYBR green probe (Takara, Japan). The RNA expression change value obtained from qPCR was expressed as a relative change of GAPDH mRNA as a standard gene compared with a non-treatment group (FIGS. 7A to 7C). The primer sequences for mouse genes used in the test are shown in Table 4.

TABLE 4

| Gene | Direction | Nucleotide Sequence (5' to 3') | SEQ ID NO |
|---|---|---|---|
| GAPDH | Forward | AGCCTCGTCCCGTAGACAA | 1 |
|  | Reverse | AATCTCCACTTTGCCACTGC | 2 |
| IL-6 | Forward | TTGGTCCTTAGCCACTCCTTC | 3 |
|  | Reverse | TAGTCCTTCCTACCCCAATTTCC | 4 |
| IL-1β | Forward | TGTGCAAGTGTCTGAAGCAGC | 5 |
|  | Reverse | TGGAAGCAGCCCTTCATCTT | 6 |
| iNOS | Forward | CGAAACGCTTCACTTCCAA | 7 |
|  | Reverse | TGAGCCTATATTGCTGTGGCT | 8 |

As shown in FIGS. 7A to 7C, the production of the inflammation factors IL-6, IL-1β, and iNOS significantly increased in the Raw 264.7 macrophages by LPS treatment (negative control group), and in the test group treated with the complex extract of three kinds of herbal medicines in Preparative Example 1 at concentrations of 0.5, 1, and 2 mg/ml together with LPS, all the expression levels of IL-6, IL-1β, and iNOS were significantly reduced in a dose-dependent manner. It can be therefore seen that the complex extract of three kinds of herbal medicines of the present disclosure showed an excellent anti-inflammatory effect.

Figure 8:
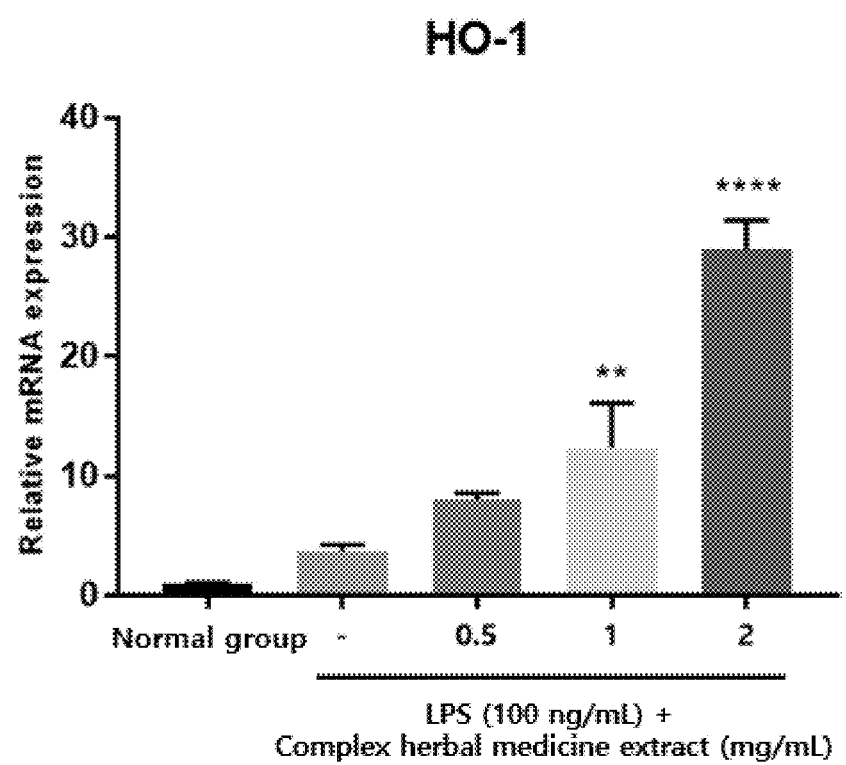
FIG. 8 is a graph comparing the expression levels of the antioxidative factor HO-1 according to the treatment concentrations (0, 0.5, 1, 2 mg/ml) of the complex herbal medicine extract in mouse macrophage cell line treated with LPS, in order to investigate the antioxidative effect of the complex herbal medicine extract of the present disclosure.

Test Example 8: Antioxidative Factor Expression Increasing Effect (Antioxidative Effect) of Complex Herbal Medicine Extract in Macrophage Cell Line Treated With LPS In order to investigate the effect of the complex herbal medicine extract of the present disclosure on the expression of the antioxidative factor heme oxygenase-1 (HO-1) in the macrophage cell line induced by LPS, the test was carried out by the same method as in Test Example 7 except that qPCR was performed by using primers specific to HO-1 gene and SYBR green probe (Takara, Japan). The RNA expression change value obtained from the qPCR results was expressed as a relative change of GAPDH mRNA as a standard gene compared with a non-treatment group (FIG. 8). The primer sequences for mouse genes used in the test are shown in Table 5.

TABLE 5

| Gene | Direction | Nucleotide Sequence (5' to 3') | SEQ ID NO |
|---|---|---|---|
| GAPDH | Forward | AGCCTCGTCCCGTAGACAA | 1 |
|  | Reverse | AATCTCCACTTTGCCACTGC | 2 |
| HO-1 | Forward | CAGGTGATGCTGACAGAGGA | 9 |
|  | Reverse | GAGAGTGAGGACCCACTGGA | 10 |

As shown in FIG. 8, in the test group treated with the complex herbal medicine extract in Preparative Example 1 at concentrations of 0.5, 1, and 2 mg/ml together with LPS, the expression level of HO-1 significantly increased in a dose-dependent manner. It can be therefore seen that the complex herbal medicine extract of the present disclosure showed an excellent anti-oxidative effect.

Test Example 9: Antioxidative Factor Expression Increasing Effect (Antioxidative Effect) of Complex Herbal Medicine Extract According to Mixing Ratio of Herbal Medicines in Macrophage Cell Line Treated With LPS In order to investigate an antioxidative effect of the complex herbal medicine extract in Preparative Example 2 according to the mixing ratio in the Raw 264.7 macrophage cell line induced by LPS, qPCR was performed by using the primers specific to HO-1 gene and the SYBR green probe (Takara, Japan). The detailed test procedure was the same as in Test Example 8, and the primer sequences for the mouse genes used in the test are shown in Table 5 above.

Figure 9:
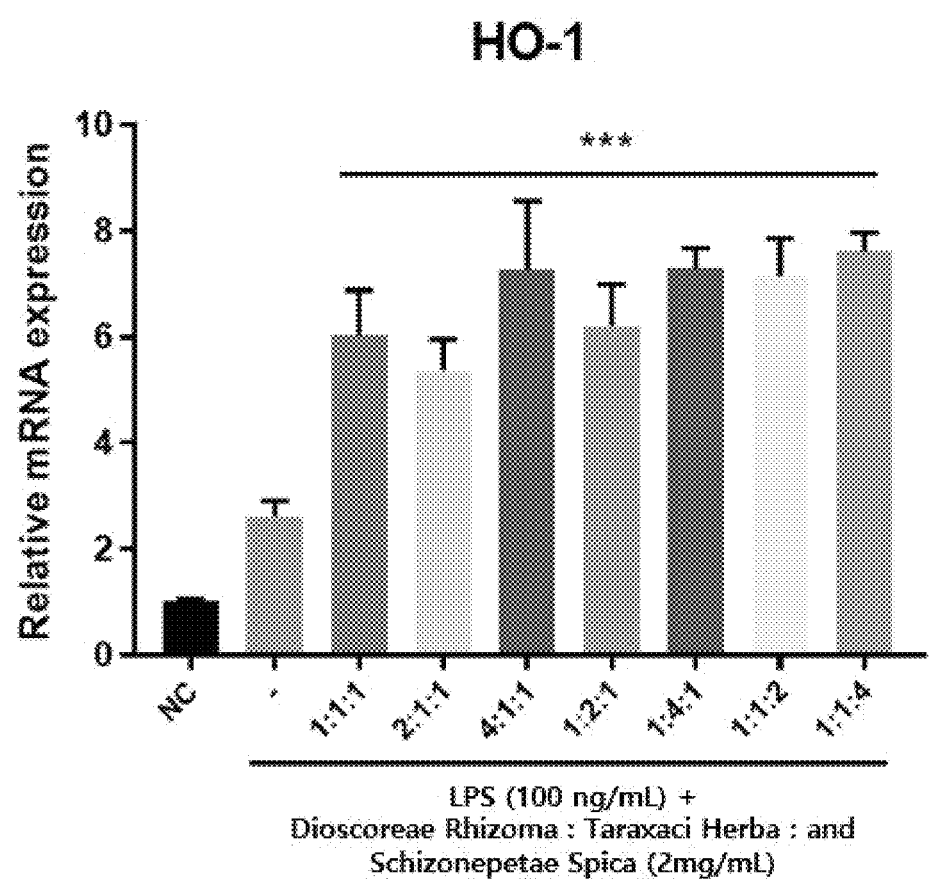
FIG. 9 is a graph comparing the expression levels of the antioxidative factor HO-1 according to various ratios of herbal medicines in mouse macrophage cell line treated with LPS, in order to investigate the antioxidative effect according to the mixing ratio in the complex herbal medicine extract of the present disclosure.

As shown in FIG. 9, all the test groups treated with the complex herbal medicine extracts in Preparative Example 2 at a concentration of 2 mg/ml together with LPS showed an excellent antioxidative effect by significantly increasing the expression level of the antioxidative factor HO-1.

Test Example 10: Anti-Inflammatory and Antioxidative Effects of Complex Herbal Medicine Extract According to Concentration of Extraction Solvent (Ethanol) in Macrophage Cell Line Treated With LPS In order to investigate the anti-inflammatory and antioxidative effects of the complex herbal medicine extracts according to the concentrations of the extraction solvent (ethanol) in Preparative Example 3 and the hot-water complex herbal medicine extract in Preparative Example 4, qPCR was performed by using the primers specific to iNOS, and HO-1 and the SYBR green probe (Takara, Japan). Each of the extracts was used at a concentration of 2 mg/ml. The detailed test procedures were the same as in Test Examples 7 and 8, and the primer sequences for the mouse genes used in the tests are shown in Tables 4 and 5 above.

Figure 10:
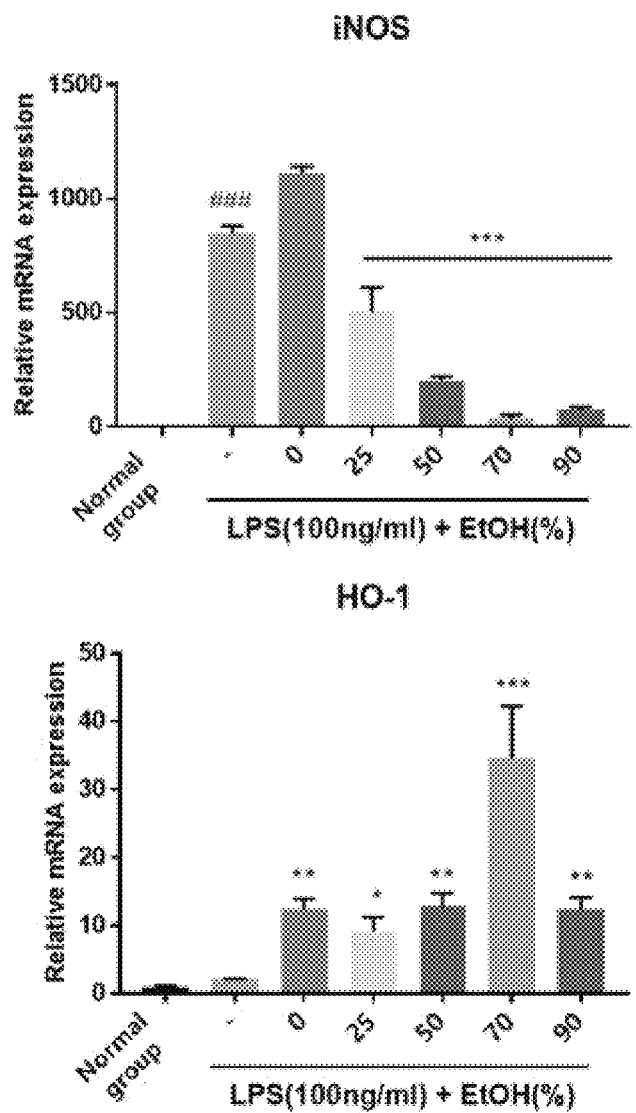
FIG. 10 illustrates graphs comparing the expression levels of the inflammatory factor (iNOS) and the expression levels of the antioxidative factor HO-1 according to the extraction method (hot-water extraction, 0%) and the concentrations (25, 50, 70, and 90%) of the extraction solvent (ethanol) in the mouse macrophage cell line treated with LPS, in order to investigate the anti-inflammatory effect and the antioxidative effect according to the extraction method (hot-water extraction) of the complex herbal medicine extract and the concentrations of the extraction solvent (ethanol) of the present disclosure.

As shown in FIG. 10, the complex herbal medicine extracts according to the concentrations of the extraction solvent (ethanol) prepared in Preparative Example 3 significantly reduced the expression of iNOS increased by LPS treatment, showing an excellent anti-inflammatory effect. In addition, all the complex herbal medicine extracts in Preparative Examples 3 and 4 significantly increased the expression level of the antioxidative factor HO-1, showing an excellent antioxidative effect.

Test Example 11: Anti-Inflammatory Effects of Single Herbal Medicine Extract and Complex Herbal Medicine Extract in Pulmonary Inflammation Mouse Model Induced by LPS In order to investigate the pulmonary inflammation inhibitory effect of single and complex herbal medicine extracts, the following test was carried out. After 7-week-old male C57BL/6 mice (Raonbio, Korea) were acclimated for at least one week, the animals were classified into (1) a normal group, (2) a group with LPS induction and distilled water administration (negative control group), (3) to (5) groups with LPS induction and single herbal medicine extract administration, and (6) a group with LPS induction and complex herbal medicine extract administration.

The complex herbal medicine extract in Preparative Example 1 dissolved in distilled water and the single extracts of three kinds of herbal medicines in Comparative Example 1 dissolved in distilled water were orally administered to the test groups of (3) to (6) at 500 mg/kg once/day for five days, and only distilled water was orally administered to the normal group and the negative control group.

The induction of acute pulmonary inflammation in the test groups and the negative control group was performed by administering 50 µg of LPS (Sigma, US) dissolved in 50 µl of phosphate buffered saline (PBS) as a single drop into the mouse trachea 24 hours before the end of the test. For the normal group, phosphate buffered saline (PBS) was administered as a single drop into the mouse trachea.

After the last administration of the herbal medicine extracts or distilled water, the mice were sacrificed with carbon dioxide, and then the lung tissue was separated, and RNA was extracted by using TRIzol (Invitrogen, USA). Thereafter, cDNA obtained through RT-PCR was used to perform qPCR using primers specific to the inflammatory factors IL-1β, IL-6, and TNF-α and the SYBR green probe (Takara, Japan). The RNA expression change value obtained from qPCR was expressed as a relative change of GAPDH mRNA as a standard gene compared with a non-treatment group. The primer sequences for mouse genes used in the test are shown in Table 6.

TABLE 6

| Gene | Direction | Nucleotide Sequence (5' to 3') | SEQ ID NO |
|---|---|---|---|
| GAPDH | Forward | AGCCTCGTCCCGTAGACAA | 1 |
|  | Reverse | AATCTCCACTTTGCCACTGC | 2 |
| IL-6 | Forward | TTGGTCCTTAGCCACTCCTTC | 3 |
|  | Reverse | TAGTCCTTCCTACCCCAATTTCC | 4 |
| IL-1β | Forward | TGTGCAAGTGTCTGAAGCAGC | 5 |
|  | Reverse | TGGAAGCAGCCCTTCATCTT | 6 |
| TNF-α | Forward | AAGCCTGTAGCCCACGTCGTA | 11 |
|  | Reverse | GGCACCACTAGTTGGTTGTCTTTG | 12 |

Figure 11A:
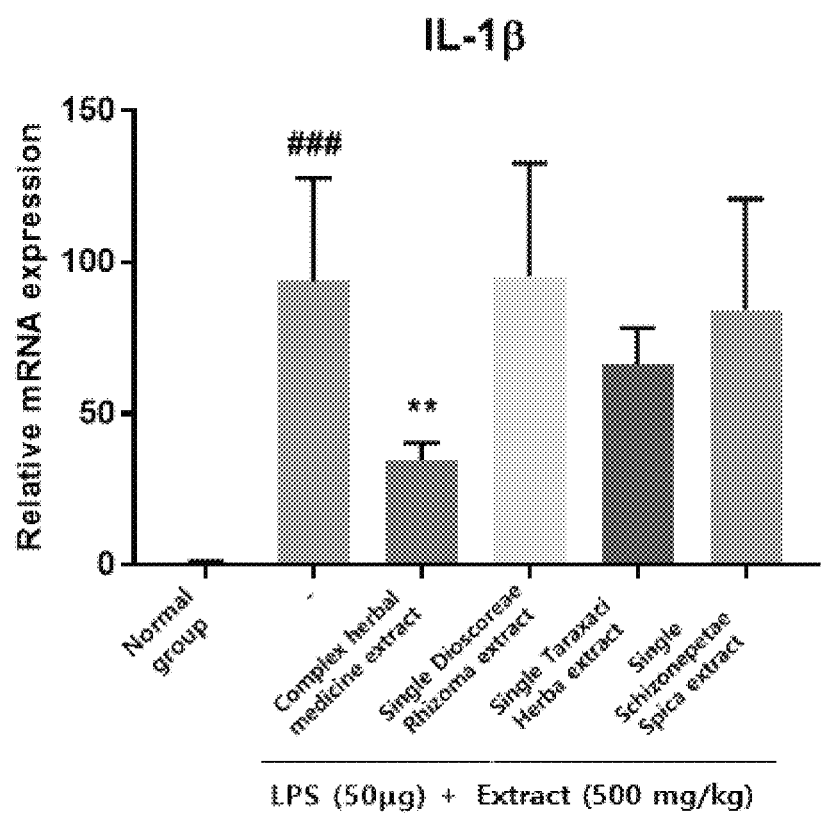
FIGS. 11A, 11B and 11C are graphs comparing the expression levels of the inflammatory factors (IL-1β, IL-6, and TNF-α) according to the treatment with the single extracts of herbal medicines (Dioscoreae Rhizoma, Taraxaci Herba, and Schizonepetae Spica) and the complex herbal medicine extract in the pulmonary inflammation mouse models induced by LPS, in order to investigate the pulmonary inflammation inhibitory effect of the single extracts and complex extract of herbal medicines.
Figure 11B:
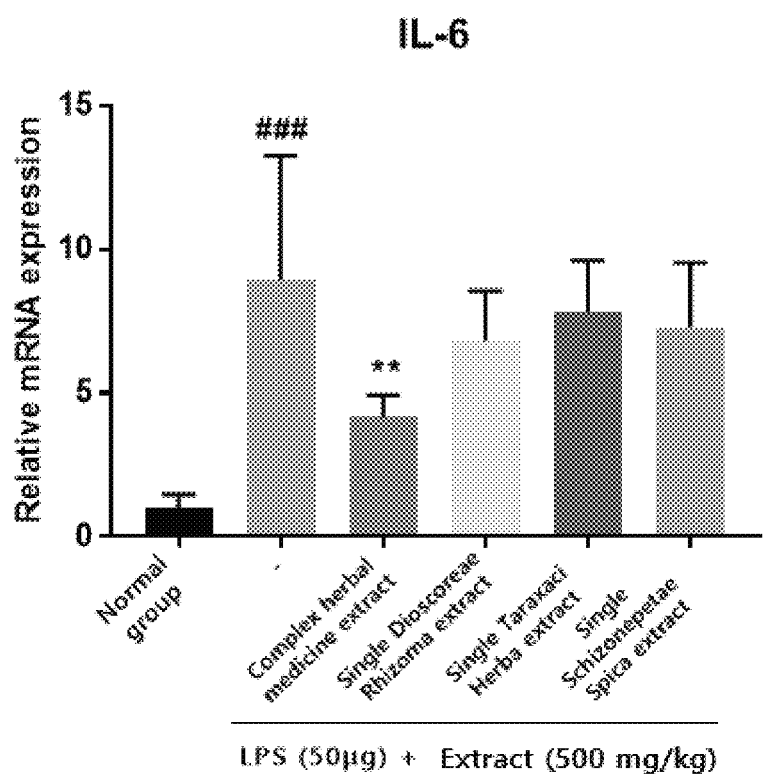
Figure 11C:
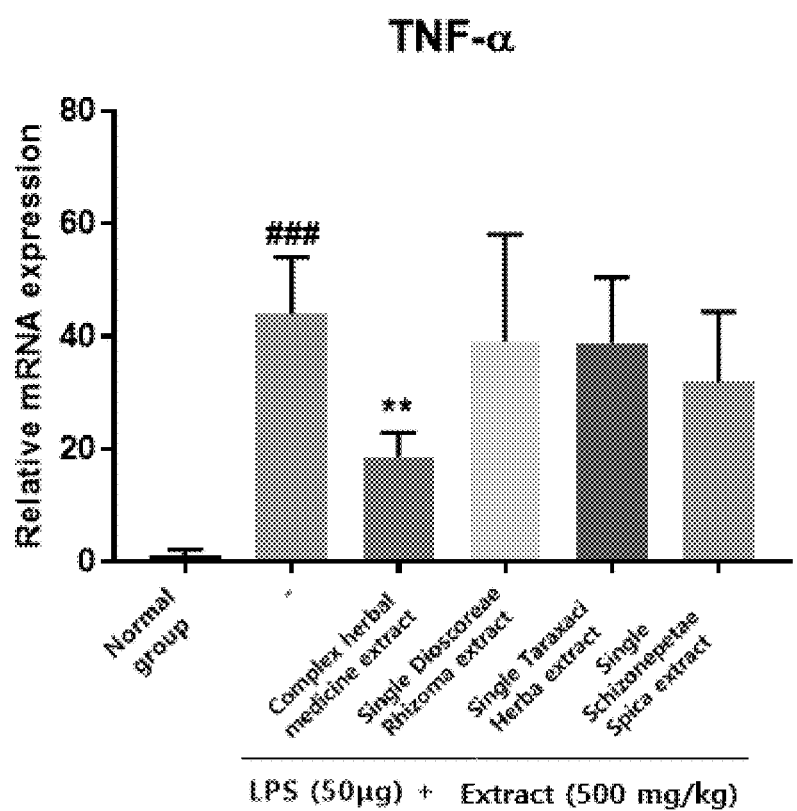

As shown in FIGS. 11A to 11C, the expression of the inflammatory factors IL-1β, IL-6, and TNF-α within the lung tissue was increased by LPS. The administration of each of the single extracts of three kinds of herbal medicines showed expression levels of the inflammatory factors similar to those in the negative control group. Whereas, the complex herbal medicine extract reduced the expression of the inflammatory factors to significant levels compared with the negative control group, thereby showing a synergistic effect in the anti-inflammatory effect.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. An oral composition consisting of a mixed extract of Dioscoreae Rhizoma, Taraxaci Herba, and Schizonepetae Spica, and (b) a pharmaceutically acceptable carrier,
   wherein the Dioscoreae Rhizoma, Taraxaci Herba, and Schizonepetae Spica are in a weight ratio of 1-4:1:1-4 or 1:1-4:1-4,
   wherein the extract is obtained by extraction with C1 to C6 lower alcohol or aqueous solution thereof, and
   wherein the oral composition is selected from the group consisting of an emulsion, granules, a tablet, and a capsule.

2. The composition of claim 1, wherein the C1 to C6 lower alcohol is ethanol.

3. A method for alleviation or treatment of a respiratory disease comprising:
   administering a composition to a subject in need thereof, the composition consisting of a mixed extract of Dioscoreae Rhizoma, Taraxaci Herba, and Schizonepetae Spica,
   wherein the Dioscoreae Rhizoma, Taraxaci Herba, and Schizonepetae Spica are in a weight ratio of 1-4:1:1-4 or 1:1-4:1-4,
   wherein the extract is obtained by extraction with C1 to C6 lower alcohol or aqueous solutions thereof, and
   wherein the respiratory disease is selected from the group consisting of rhinitis, pharyngitis, laryngitis, pharyngolaryngitis, pneumonia, acute or chronic bronchitis, and chronic obstructive pulmonary disease.

4. The method of claim 3, wherein the C1 to C6 lower alcohol is alcohol.

* * * * *

SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Forward primer for GAPDH

<400> SEQUENCE: 1
agcctcgtcc cgtagacaa                                                19

<210> SEQ ID NO 2
<211> LENGTH: 20

```
<212> TYPE: DNA
<213> ORGANISM: Artificial Sequence
<220> FEATURE:
<223> OTHER INFORMATION: Reverse primer for GAPDH

<400> SEQUENCE: 2
aatctccact ttgccactgc                                                 20

<210> SEQ ID NO 3
<211> LENGTH: 21
<212> TYPE: DNA
<213> ORGANISM: Artificial Sequence
<220> FEATURE:
<223> OTHER INFORMATION: Forward primer for IL-6

<400> SEQUENCE: 3
ttggtcctta gccactcctt c                                               21

<210> SEQ ID NO 4
<211> LENGTH: 23
<212> TYPE: DNA
<213> ORGANISM: Artificial Sequence
<220> FEATURE:
<223> OTHER INFORMATION: Reverse primer for IL-6

<400> SEQUENCE: 4
tagtccttcc taccccaatt tcc                                             23

<210> SEQ ID NO 5
<211> LENGTH: 21
<212> TYPE: DNA
<213> ORGANISM: Artificial Sequence
<220> FEATURE:
<223> OTHER INFORMATION: Forward primer for IL-1beta

<400> SEQUENCE: 5
tgtgcaagtg tctgaagcag c                                               21

<210> SEQ ID NO 6
<211> LENGTH: 20
<212> TYPE: DNA
<213> ORGANISM: Artificial Sequence
<220> FEATURE:
<223> OTHER INFORMATION: Reverse primer for IL-1beta

<400> SEQUENCE: 6
tggaagcagc ccttcatctt                                                 20

<210> SEQ ID NO 7
<211> LENGTH: 19
<212> TYPE: DNA
<213> ORGANISM: Artificial Sequence
<220> FEATURE:
<223> OTHER INFORMATION: Forward primer for iNOS

<400> SEQUENCE: 7
cgaaacgctt cacttccaa                                                  19

<210> SEQ ID NO 8
<211> LENGTH: 21
<212> TYPE: DNA
<213> ORGANISM: Artificial Sequence
<220> FEATURE:
<223> OTHER INFORMATION: Reverse primer for iNOS

<400> SEQUENCE: 8
```

```
tgagcctata ttgctgtggc t                                            21

<210> SEQ ID NO 9
<211> LENGTH: 20
<212> TYPE: DNA
<213> ORGANISM: Artificial Sequence
<220> FEATURE:
<223> OTHER INFORMATION: Forward primer for HO-1

<400> SEQUENCE: 9
caggtgatgc tgacagagga                                              20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for HO-1

<400> SEQUENCE: 10
gagagtgagg acccactgga                                              20

<210> SEQ ID NO 11
<211> LENGTH: 21
<212> TYPE: DNA
<213> ORGANISM: Artificial Sequence
<220> FEATURE:
<223> OTHER INFORMATION: Forward primer for TNF-alpha

<400> SEQUENCE: 11
aagcctgtag cccacgtcgt a                                            21

<210> SEQ ID NO 12
<211> LENGTH: 24
<212> TYPE: DNA
<213> ORGANISM: Artificial Sequence
<220> FEATURE:
<223> OTHER INFORMATION: Reverse primer for TNF-alpha

<400> SEQUENCE: 12
ggcaccacta gttggttgtc tttg                                         24
```